(12) United States Patent
Barry

(10) Patent No.: US 8,061,606 B2
(45) Date of Patent: Nov. 22, 2011

(54) METHOD AND SYSTEM FOR MULTIPLE IDENTIFIERS ASSOCIATION

(75) Inventor: Fabien Barry, Ollioules (FR)

(73) Assignee: Psion Teklogix, Inc., Ontario (CA)

( * ) Notice: Subject to any disclaimer, the term of this patent is extended or adjusted under 35 U.S.C. 154(b) by 250 days.

(21) Appl. No.: 12/469,975

(22) Filed: May 21, 2009

(65) Prior Publication Data

US 2010/0294840 A1 Nov. 25, 2010

(51) Int. Cl.
*G06K 7/015* (2006.01)
(52) U.S. Cl. ........ 235/435; 235/380; 235/439; 235/440; 235/459
(58) Field of Classification Search ..... 235/435–462.01; 340/572.1
See application file for complete search history.

(56) References Cited

U.S. PATENT DOCUMENTS

| | | | |
|---|---|---|---|
| 5,962,834 A * | 10/1999 | Markman | 235/385 |
| 6,371,375 B1 * | 4/2002 | Ackley et al. | 235/462.45 |
| 7,073,712 B2 * | 7/2006 | Jusas et al. | 235/451 |
| 7,554,449 B2 * | 6/2009 | Higham | 340/572.1 |
| 2005/0036097 A1 | 2/2005 | Satake | |
| 2006/0289654 A1 * | 12/2006 | Robinson et al. | 235/462.46 |
| 2007/0017997 A1 | 1/2007 | Talley et al. | |
| 2008/0122623 A1 * | 5/2008 | Hause et al. | 340/572.1 |
| 2009/0295545 A1 * | 12/2009 | O'Haire et al. | 340/10.5 |
| 2009/0321525 A1 * | 12/2009 | Barkan | 235/472.01 |
| 2011/0062237 A1 * | 3/2011 | Chaves | 235/454 |

* cited by examiner

*Primary Examiner* — Thien M. Le
*Assistant Examiner* — Christle Marshall
(74) *Attorney, Agent, or Firm* — Brinks Hofer Gilson & Lione

(57) ABSTRACT

A method and system for managing a physical object is provided. The system includes a RFID module for reading RFID tag information from a RFID tag in a RFID tag reading area, a handheld terminal being operable as a stand-alone device, a docking station for operably coupling the handheld terminal to the RFID module, and a storage for holding a physical object having the barcode and the RFID tag to locate the physical object in the barcode reading area and the RFID tag reading area. The method uses a system having a RFID module, a handheld terminal having a barcode scanner and being operable as a stand-alone device, a docking station for operably coupling the handheld device to the RFID module, and a storage for holding the physical object having a barcode and a RFID tag, the handheld device driving the RFID module via the docking station.

26 Claims, 8 Drawing Sheets

METHOD AND SYSTEM FOR MULTIPLE IDENTIFIERS ASSOCIATION

FIELD

The present invention relates to item tagging technologies, and more specifically to a system for associating a plurality of indicia allocated to an object.

BACKGROUND

The statements in this section merely provide background information related to the present disclosure and may not constitute prior art.

RFID tags and barcode labels are used in a variety of applications, such as tracking physical objects, inventory management, warehouse operations. For example, a RFID tag having a memory chip is programmed to encode information on an object, and is allocated to the object. A barcode label having information on the object is printed on the surface of the object.

Typically, a RFID printer is used to print a RFID label on the surface of the object and encode information to a tag embedded into the label with the same ID number. However, in many applications, tags are not printable. Such applications include, for example, but not limited to, those using tags embedded into the object or those using tags with rugged packages. In these applications, an object is positioned so that a barcode label printed on the object is scanned by the barcode scanner, and then the object is relocated so that a tag allocated to the object is read by the RFID reader subsequently. The barcode label information and the tag information will be associated after these operations. The barcode label and the RFID tag association takes time since it requires manually moving the object to read and associate the barcode label and the RFID tag, and there is a high risk of error in the association process.

SUMMARY

The present disclosure provides a method and system that obviates or mitigates at least one of the disadvantages of existing systems.

According to an aspect of the present disclosure there is provided a system for managing a physical object, which includes: a RFID module for reading RFID tag information from a RFID tag in a RFID tag reading area; a handheld terminal being operable as a stand-alone device, including: a barcode scanner for reading barcode information from a barcode in a barcode reading area; a driver for driving the RFID module; and a module for associating the barcode information with the RFID tag information transferred from the RFID module; a docking station for operably coupling the handheld terminal to the RFID module; and a storage for holding a physical object having the barcode and the RFID tag to locate the physical object in the barcode reading area and the RFID tag reading area.

According to another aspect of the present disclosure there is provided a method of managing a physical object using a system having a RFID module, a handheld terminal having a barcode scanner and being operable as a stand-alone device, a docking station for operably coupling the handheld device to the RFID module, and a storage for holding the physical object having a barcode and a RFID tag, the handheld device driving the RFID module via the docking station. The method includes: determining a barcode reading area of the barcode scanner; determining a RFID tag reading area of the RFID module; determining a position of the physical object in the storage, based on the barcode reading area and the RFID tag reading area; operating the handheld terminal to read barcode information from the barcode in the position by the barcode scanner; operating the RFID module by the handheld terminal via the docking station to read RFID tag information from the RFID tag in the position; and operating the handheld terminal to associate the barcode information and the RFID tag information.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

The drawings described herein are for illustration purposes only and are not intended to limit the scope of the present disclosure in any way.

DETAILED DESCRIPTION

The following description is merely exemplary in nature and is not intended to limit the present disclosure, application, or uses.

Figure 1:
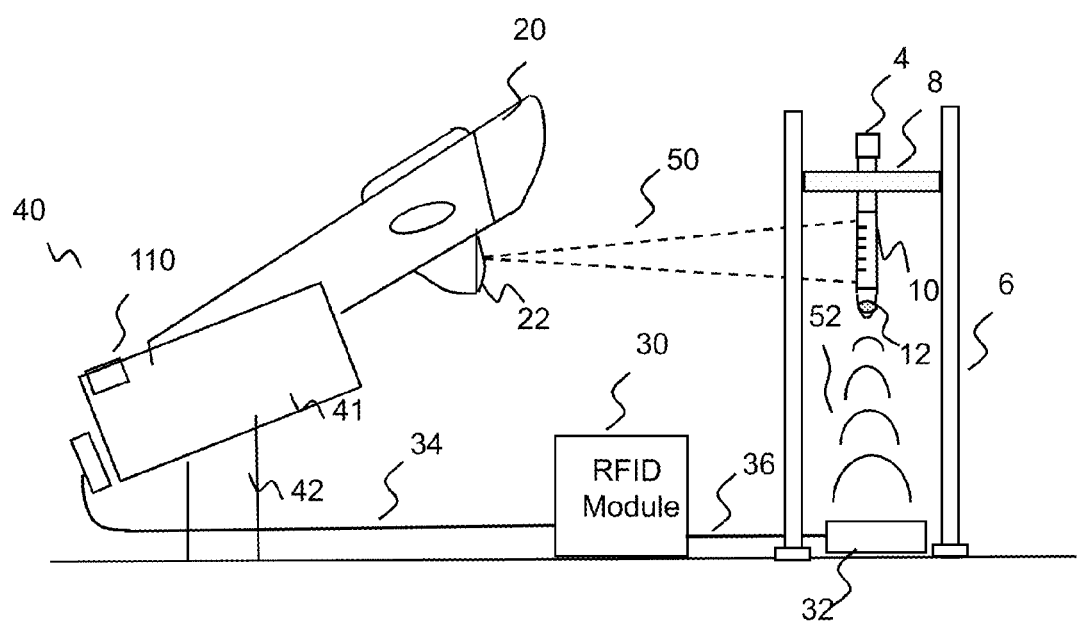
FIG. 1 is a side view illustrating an example of a system for managing a physical object with multiple identifiers, having a storage, a handheld terminal, a docking station and a RFID reader.
Figure 2:
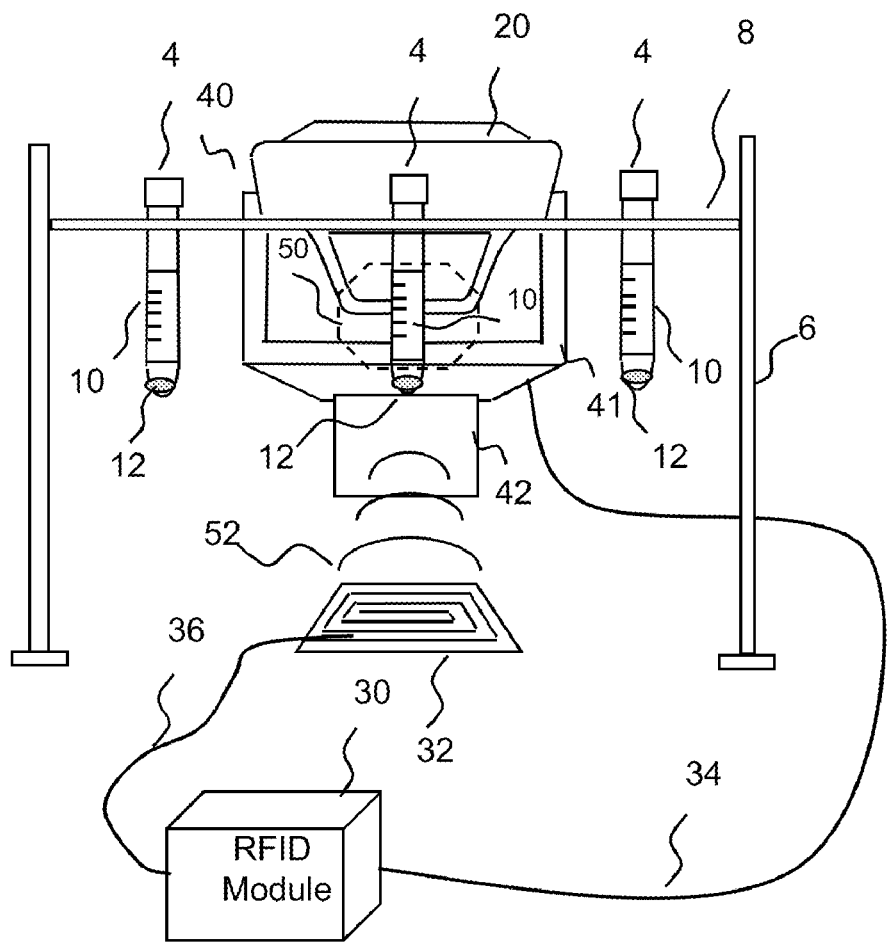
FIG. 2 is a front view illustrating the system of FIG. 1.

Referring to FIGS. 1-2, an example of a system for managing a physical object with multiple identifiers is described. The system 2 of FIGS. 1-2 is an ergonomic system that provides natural and easy operations to read and associate the multiple identifiers allocated to the physical object. In FIGS. 1-2, a cryotube 4 is shown as an example of the physical object.

The cryotube 4 is a sterile tube for the storage of biological samples and placed at cold temperatures. A plurality of identifiers are allocated to the cryotube 4. In this example, a barcode label 10 and a RFID tag 12 are allocated to the cryotube 4. The barcode label 10 is attached to the side of the cryotube 4. A barcode is printed on the label 10. The RFID tag 12 is placed in the cryotube 4. In the description, the terms "barcode", "label", and "barcode label" may be used interchangeably. In the description, the terms "tag" and "RFID tag" may be used interchangeably. The system 2 simultaneously captures all information available from the barcode 10 and the RFID tag 12 allocated to the cryotube 4, and associates them in a safe and real time way.

In the drawings, the cryotube 4, the barcode label 10 and the RFID tag 12 are illustrated schematically. One of ordinary skill in the art would understand that the sizes and the shapes of the cryotube 4, the barcode label 10 and the RFID tag 12 are not limited to those illustrated in the drawings, and may vary. One of ordinary skill in the art would understand that the system 2 can adapt physical objects different from the cryotube 4. One of ordinary skill in the art would understand that the system 2 can adapt a barcode label having a dimension (size, shape) different from that of the barcode label 10 and a RFID tag having a dimension (size, shape) from that of the RFID tag 12.

The system 2 includes a storage 6, a handheld terminal 20 having a barcode scanner 22, an external RFID reader module 30, a RFID antenna 32, a docking station 40 having a base 42. The handheld terminal 20 is a stand-alone, mobile device. The handheld terminal 20 is operably coupled with the docking station 40, and can be used as a fixed equipment. The barcode scanner 22 reads barcodes. The RFID reader 30 reads RFID tags via the RFID antenna 32. The docking station 40 is a cradle for housing the handheld terminal 20 and providing an interface between the handheld terminal 20 and the RFID reader 30. The docking station 40 allows communication between the handheld terminal 20 and the external RFID reader 30. The handheld terminal 20 drives the RFID reader 30 via the docking station 40. The docking station 40 has a connector for connecting to an external power source. Operation power is supplied to the handheld terminal 20 and the RFID reader 30 via the docking station 40.

The user operates the handheld terminal 20 to collect barcode information and RFID tag information from the cryotube 4 and associate them. The user does not need to hold the handheld terminal 20 during the barcode and RFID tag information collection (capturing) and association operation when using the docking station 40. In the description, the terms "operator" and 'user" may be used interchangeably.

The RFID reader 30 is operably connected to the docking station 40 via a cable 34. The cable 34 is a flexible cable. The RFID reader 30 communicates with the handheld terminal 20 via the cable 34 and the docking station 40. The RFID reader 30 is driven by the user of the handheld terminal 20. Power is supplied from the docking station 40 to the RFID reader 30 via the cable 34. There is no battery life time/power consideration about the RFID reader 30 since the RFID reader 30 is fed by the docking station 40.

The RFID reader 30 is coupled with the RFID antenna 32 via a cable 36. The cable 36 is a flexible cable, and thus the position of the RFID antenna 32 is changeable. The RFID reader 30 provides antenna power to the RFID antenna 32 via the cable 36. The radiated Electro Magnetic Field by the RFID antenna 32 is adjusted based on the handheld terminal's command(s).

The barcode scanner 22 defines a barcode scanning (reading) area 50. The barcode scanner 22 scans the barcode label 10 in the barcode reading area 50.

The dimension (e.g., size, shape) of the RFID antenna 32 defines a RFID antenna coverage (RFID reading) area 52 and the performance of RFID reading. The RFID reading area 52 also varies in dependence upon antenna power. The system 2 is capable of selecting the output power of the RFID reader 30 (i.e., antenna power of the RFID antenna 32) via the handheld terminal 20 in order to adjust the RFID reading area 52. The RFID reader 30 reads tag information on the RFID tag 12 in the RFID reading area 52. In this example, the RFID antenna 32 is placed under the cryotube 4.

The storage 6 is a sample locater having one or more holders, each holding or locating the cryotube 4. Each cryotube 4 may be manually located into the holder 8. The holder 8 may be movable. The cryotube 4 is placed in a specific position defined by the barcode and RFID tag reading areas 50 and 52.

The relative position (distance, angle) of the barcode scanner 22 and the cryotube 4 in the holder 8 is predetermined so that the cryotube 4 is located in the barcode reading area 50. The relative position (distance, angle) of the RFID antenna 32 and the cryotube 4 in the holder 8 is predetermined so that the cryotube 4 is located in the RFID reading area 52. The holder 8 is arranged so that the barcode scanner 22 is located at the predetermined distance and angle from the cryotube 4 and the cryotube 4 in the holder 8 is mechanically set in the axis of the barcode scanner 22, when using the docking station 40. The operator may position the barcode label 10 of the cryotube 4 in the axis of the barcode scanner 22 so that the barcode label 10 is in the barcode reading area 50.

The docking station 40 has a docking section 41 for receiving the handheld terminal 20. The handheld terminal 20 may slide or snap into the docking section 41. One of ordinary skill in the art would understand that the size/shape of the docking section 41 of the docking station 40 may vary in dependence upon the size/shape of the handheld terminal 20. The docking section 41 for receiving the handheld terminal 20 is mounted on the base 42. The angle between the base 42 and the docking section 41 for receiving the handheld terminal 20 may be changeable.

In the drawings, some components of the system 2 are illustrated schematically. It would be well understood by one of ordinary skill in the art that the shape and size of each component of the system 2 may vary. For example, the size and shape of the storage 6 are not limited to those illustrated in the drawings, and may vary. The storage 6 may hold different types of cryotube. One of ordinary skill in the art would appreciate that the system 2 may contain components/modules/elements not illustrated in the drawings. For example, the handheld terminal 20 may include a rechargeable battery which may be chargeable through the docking station 40. The system 2 may communicate with external devices not illustrated in the drawings. In this example, the RFID reader 30 is coupled with the docking station 40 via the wired link (30). However, one of ordinary skill in the art would understand that the RFID reader 30 may be operably connected to the docking station 40 via a wireless communication network. In the description, the terms "coupling (coupled)" and "connecting (connected)" may be used interchangeably.

Figure 3:
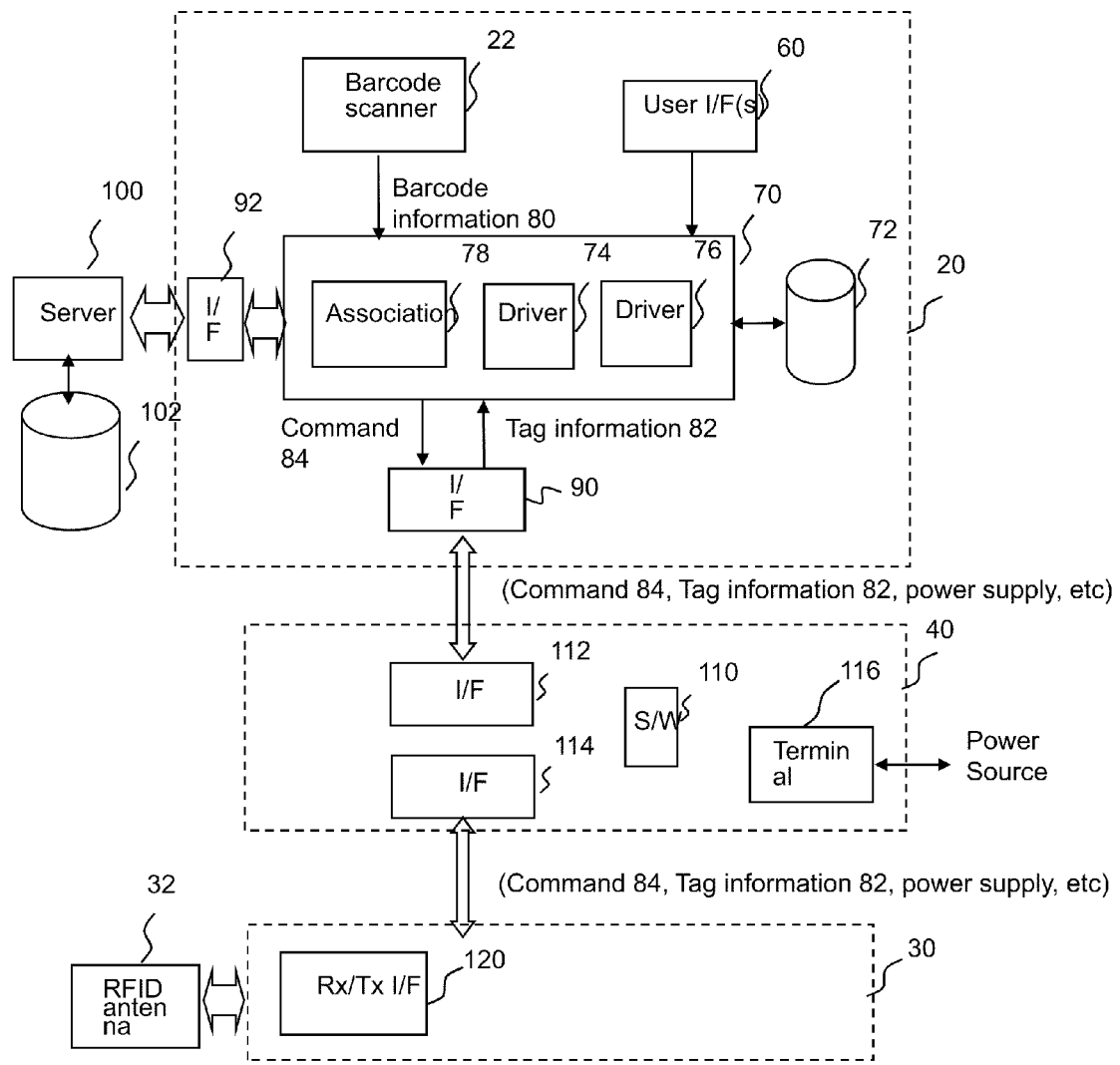
FIG. 3 is a diagram illustrating the components of the system of FIGS. 1-2.

Referring to FIG. 3, the handheld terminal 20 of FIGS. 1-2 is described in detail. The handheld terminal 20 reads barcode information 80 on the barcode label 10 via the barcode scanner 22. The barcode label 10 may be a 1D or 2D barcode label. The barcode scanner 22 may be a 1D or 2D barcode scanner. The barcode scanning operation would be well known understood by one of ordinary skill in the art.

The handheld terminal 20 has a user interface(s) (I/F) 60, such as a display (e.g., touch screen), a keyboard, a button, a switch, a speaker, and/or a visual/audio indicator. The user operates the handheld terminal 20 via the user interface 60. The user drives the processes of barcode and RFID reading and association by using the user interface 60. The antenna power depends on the RFID reader output power which is adjusted by the user interface 60. The user may select the output power from the RFID reader 30 to the RFID antenna 32 via the user interface 60.

The handheld terminal 20 includes a processor 70 and a memory 72. The processor 70 may be a general purpose processor and mounted on a main logic board. The barcode label information 80 obtained by the barcode scanner 22 is provided to the processor 70. RFID tag information 82 obtained by the RFID reader 30 is provided to the processor 70 via the docking station 40. The processor 70 is operably coupled with the user interface 60.

A plurality of modules are executed on the processor 70, which include, for example, a driving module 74 for driving the barcode scanner 22, a driving module 76 for driving the RFID reader 30, and an association module 78 for associating the barcode information 80 and the RFID tag information 82. The driving module 74 operates the barcode scanner 22 based on an input from the user interface 60. The driving module 76 generates a command(s) 84 for operating the RFID reader 30 based on an input(s) from the user interface 60. The processor 70 collects the barcode information 80 and the RFID tag information 82 allocated to the cryotube 4. The association module 78 is actuated by the user via the user interface 60. The association module 78 allows the user to make association between the barcode information 80 and the RFID tag information 82 using the user interface 60. The association between the barcode information 80 and the RFID tag information 82 may be transferred to a server 100 for further processing or tracking the cryotube 4. The handheld terminal 20 may transfer the RFID/tag information to the RFID reader 30 after establishing the association between the barcode information 80 and the RFID tag information 82.

These modules 74, 76 and 78 are, for example, software applications, and may be integrated or may interact each other.

In FIG. 3, the driving module 74, the driving module 76 and the association module 78 are in the processor 74. However, the driving module 74, the driving module 76 and/or the association module 78 may be located outside the processor 70. The association module 78 may be a graphic user interface for navigating the user to select a reading operation (collecting operation) or an association operation, and displaying information obtained by the handheld terminal 20 (e.g., the barcode information 80, the RFID tag information 82, the association result). The association module 78 may allow the user to input and/or associate other information (e.g., information on the cryotube 4) with the barcode information 80, the RFID tag information 82, and/or the association result. The driving module 74 and the driving module 76 may be graphic user interfaces, and may be included in or integrated with the association module 78.

The handheld terminal 20 includes an interface (I/F) 90 in order to log on to the docking station 40. The interface 90 allows communication with the external RFID reader 30 via the docking station 40. The handheld terminal 20 sends the commands 84 to the RFID reader 30 via the interface 90, and recovers data (e.g., tag information 82) from the RFID reader 30 via the interface 90. The handheld terminal 20 also receives power supply from the docking station 40 via the interface 90.

The handheld terminal 20 includes an interface (I/F) 92 for communicating with the server 100 having a database 102. The interfaces 92 may be implemented by electrical signaling, e.g., electrical wire signaling and/or wireless communication. Information obtained via the handheld terminal 20 (e.g., barcode information 80, tag information 82, association between the tag and barcode information) may be transferred to the server 100 for further processing, and may be stored in the database 102.

A list of expected barcodes and RFID tags may be provided from the server 100 to the handheld terminal 20 before the reading and association operations. The list of expected barcodes and RFID tags may be used to verify the barcode information 80 and the RFID tag information 84.

Referring to FIG. 3, the docking station 40 of FIGS. 1-2 is described in detail. The docking station 40 includes a switch (S/W) 110 that allows the handheld terminal 20 to be operably connected (attached) to or disconnected (released) from the docking station 40.

The docking station 40 includes an electrical signaling interface (I/F) 112 for communicating with the handheld terminal 20 and providing supply power to the handheld terminal 20. The interface 112 is operably coupled with the interface 90 of the handheld terminal via the switch 110. The commands 84 for operating RFID tag reading operation are transferred from the handheld terminal 20 to the interface 112.

The docking station 40 includes an interface (I/F) 114 for Rx/Tx communication and power supply for the external RFID reader 30. The commands 84 for operating RFID tag reading operation go over the docking station 40 and arrive to the external RFID reader 30.

The docking station 40 has a terminal 116 connectable to an external power supply source. A power is supplied to the handheld terminal 20 and the RFID reader 30 via the docking station 40 when they are coupled with the docking station 40.

The commands 84 for operating the RFID reader 30 includes a command for adjusting the antenna power of the RFID antenna 32, which is transferred from the handheld terminal 20 (e.g., driving module 72) to the external RFID reader 30 via the docking station 40. The external RFID reader 30 changes the output power to the RFID antenna 32 based on the command.

Referring to FIG. 3, the RFID reader 30 of FIGS. 1-2 is described in detail. The RFID reader 30 includes a Rx/Tx interface (I/F) 120. The RFID reader 30 communicates with the handheld terminal 20 via the Rx/Tx interface 120. The RFID reader 30 connects to the RFID antenna 32 via the Rx/Tx interface 120. The RFID reader 30 is driven by the command(s) 84 from the handheld terminal 20. The RFID tag information 82 read by the RFID reader 30 is transferred to the docking station 40 via the Rx/Tx interface 120, and is then transferred to the handheld terminal 20. The RFID reader 30 receives, via the Rx/Tx interface 120, power supply for operating the components of the RFID reader 30 and the RFID antenna 32. The tag reading operation via the RFID antenna 32 would be well known understood by one of ordinary skill in the art.

The cable 34 of FIGS. 1-2 is connected to the interface 114 of the docking station 40 and the interface 120 of the RFID reader 30. The cable 36 of FIGS. 1-2 is connected to the interface 120 of the RFID reader 30 and the RFID antenna 32. The Rx/Tx interface 120 includes a 50 ohm output for the RFID antenna 32. In this case, the cable 36 is a 50 ohms cable that can be more than 1 meter in length. The RFID reader 30 has low power consumption.

In this example, the RFID reader 30 is a RFID reader, such as a HF RFID reader for frequency 13.56 MHz. In another example, the RFID reader 30 may be a RFID reader/writer that can write information on the chip of the RFID tag 12 and read the tag information 82 from the RFID tag 12. The RFID reader 30 may receive, from the handheld terminal 20, information that is to be encoded into the RFID tag 12.

The RFID antenna 32 may be, for example, a HF antenna, a LF antenna or a UHF antenna. The RFID antenna 32 size may be, for example, about 5 cm×5 cm, and may be made of a flexible printed circuit board.

Figure 4:
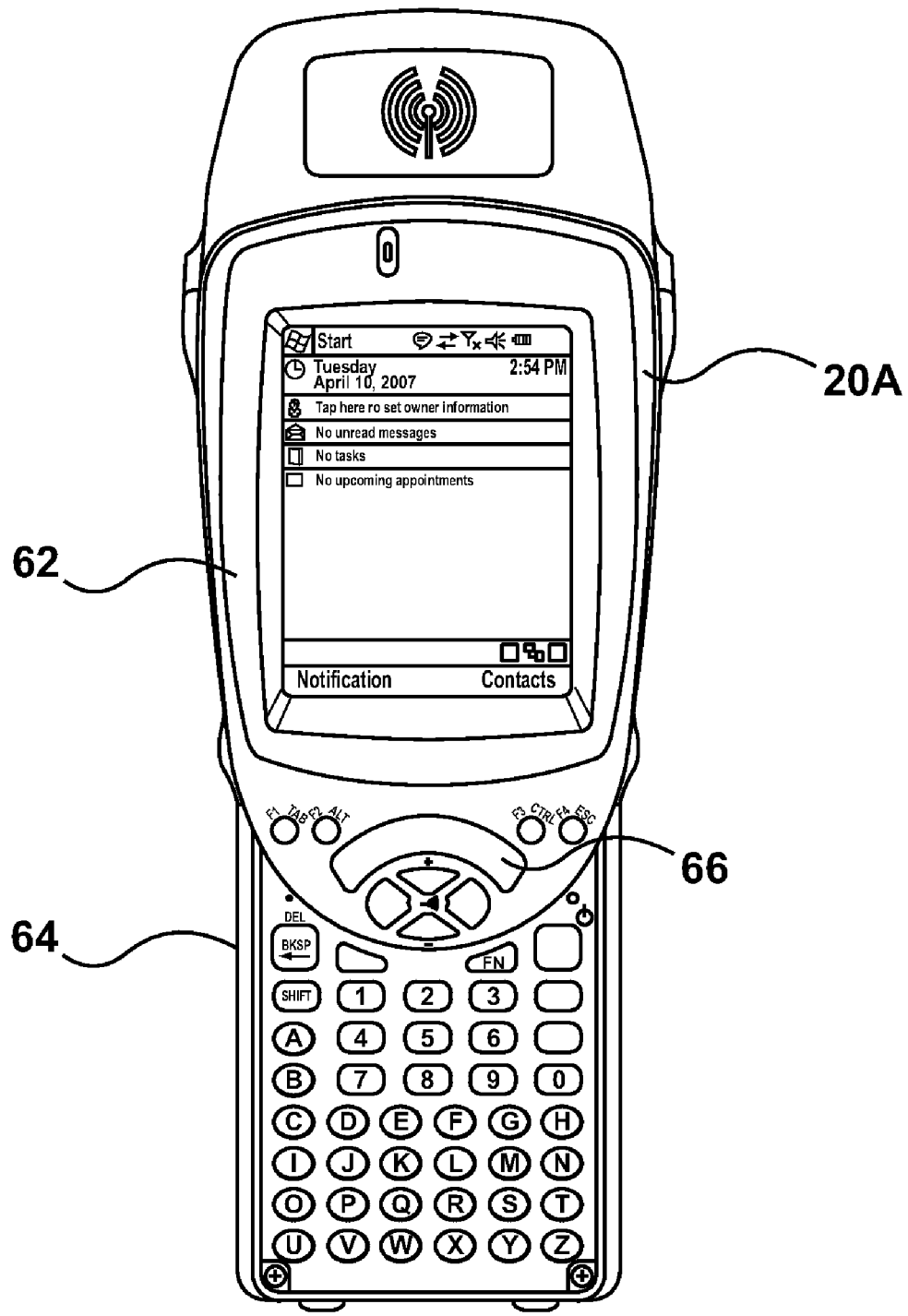
FIG. 4 is a diagram illustrating one example of the handheld terminal of FIGS. 1-2.

Referring to FIG. 4, one example of the handheld terminal 20 is described. The handheld terminal 20A of FIG. 4 is one example of the handheld terminal 20 of FIGS. 1-2 and includes a plurality of user interfaces, such as a display screen 62 (e.g., touch screen), a keyboard 64, buttons/switches 66. The handheld terminal 20A may have other user interfaces, such as, a speaker, and/or a visual/audio indicator. These interface components 62, 64, and 66 communicate with the processor 70 of FIG. 3. The display screen 62 may display a menu for navigating the user to select an operation (e.g., the barcode reading operation, the RFID tag reading operation, and the association operation), and associate the barcode information 80 with the RFID tag information 82. The buttons/switches 66 may include actuators for actuating some operations, such as the barcode reading operation and/or the RFID tag reading operation.

Figure 5:
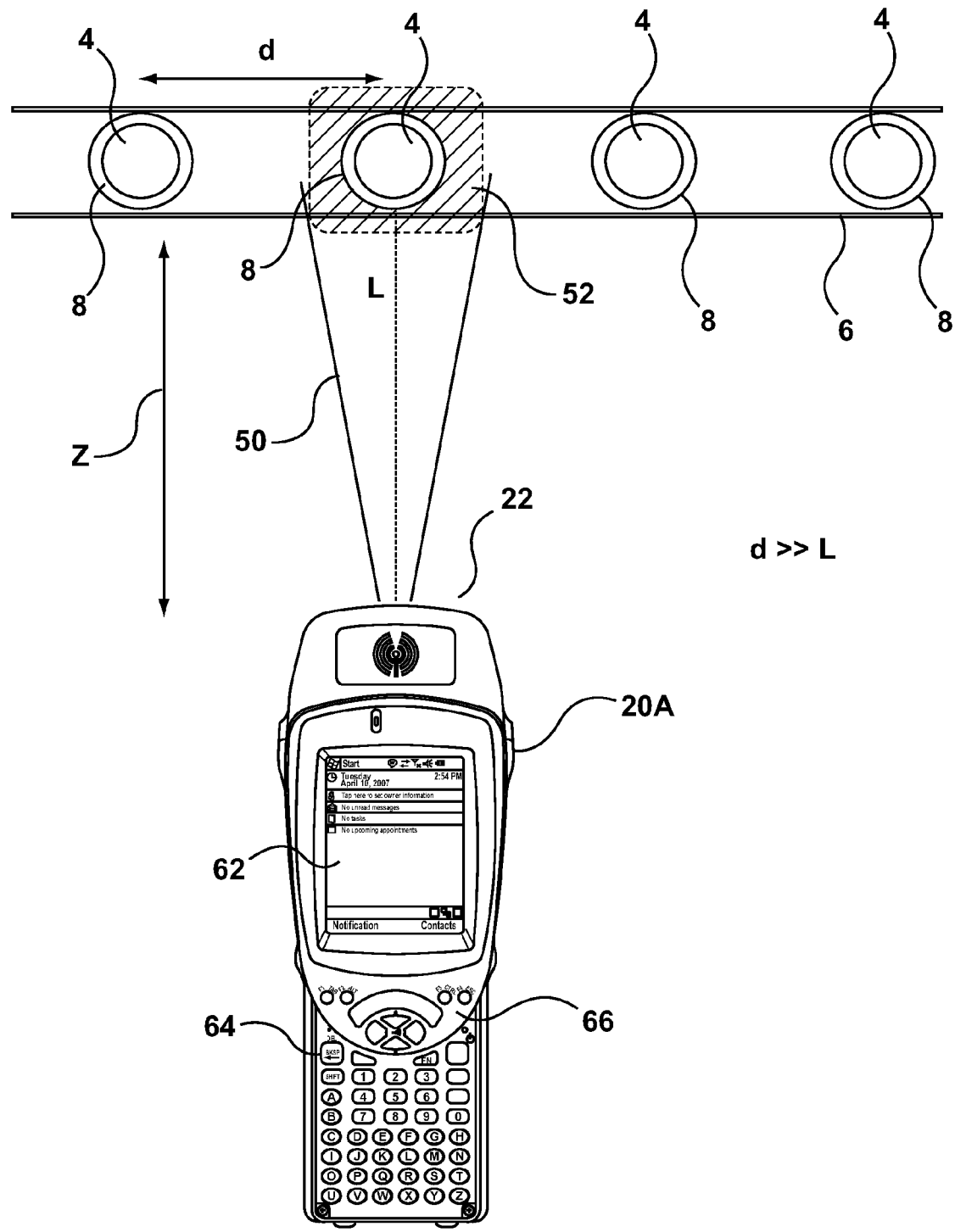
FIG. 5 is a diagram illustrating a relationship among reading areas and the storage of FIGS. 1-2.

Referring to FIGS. 1-5, one example of a relationship among the barcode reading area 50, the RFID reading area 52 and the storage 6 is described in detail. In FIG. 5, the handheld terminal 20A of FIG. 4 is used as one component of the system 2 of FIG. 1. In FIG. 5, the docking station 40 of FIG. 1 is not illustrated, however, it is assumed that the handheld terminal 20A is docked into the docking station 40. In FIG. 5, the RFID reading area 52 has a width L in a longitudinal direction. In FIG. 5, the barcode scanning area 50 covers the cryotube 4 in the holder 8, and has a width L at the holder 8. The barcode scanning area 50 and the RFID reading area 52 may have different sizes.

The distance Z between the cryotube 4 and the barcode scanner 22 and the aperture angle of the barcode scanner 22 are predetermined in order to scan a barcode label 10 in a specific position only, and not read neighbor labels. The distance Z may vary in dependence upon the size of the barcode label 10. The holder 8 is placed at the distance Z from the barcode scanner 22.

With respect to the RFID reading area 52, the antenna reading distance is controlled and adjusted, for example, to a few centimeters, in order to read a RFID tag 12 in the specific position only, and not read neighbor tags. The antenna reading distance is adjusted, for example, by controlling the output power of the RFID reader 30. The position of the RFID antenna 32 itself is changeable by using the cable 36.

The holders 8 of the storage 6 are spaced each other with a distance d in a longitudinal direction. The interspaces d between each holder 8 are calculated so that the system 2 does not read tags or barcode labels, other than a specific tag and a specific barcode label of the cryotube 4 in the specific position. The distance d is large enough to meet d>>L.

Referring to FIG. 1-6, one example of the RFID and barcode association process is described in detail. The RFID and barcode association is activated 130 by the user of the system 2. It may be activated via the user interface 60 of the handheld terminal (20, 20A). In this example, the association process is implemented using a graphic user interface. The driving modules 74 and 76 and the association module 78 may be executed for the RFID and barcode association process of FIG. 6.

A menu of the association process is displayed on the screen (62 of FIG. 4). The menu includes, for example, a plurality of icons for allowing the user to select operations, such as barcode reading operation 132, RFID tag reading operation 136 and association operation 142.

In this example, the user selects the barcode reading operation 132 from the menu. The barcode reading operation 132 is implemented by the barcode scanner 22. The result of the barcode reading operation 132 (e.g., barcode information 80) may be displayed on the screen (62 of FIG. 4) of the handheld terminal 20. If the barcode is not read or the barcode reading operation 132 is interrupted, the barcode reading operation 132 may be selected again (e.g., 134). The result of the barcode reading operation 132 may be stored in the memory 72 of the handheld terminal 20.

In this example, after the barcode reading operation 132, the user selects the RFID tag reading operation 136 from the menu. The RFID tag reading operation 136 may be selected automatically. The RFID tag reading operation 136 is driven by the handheld terminal 20 and implemented by the RFID reader 30. The result of the RFID tag reading operation 136 (e.g., tag information 82) may be displayed on the screen (62 of FIG. 4) of the handheld terminal. If the RFID tag is not read or the RFID tag reading operation is interrupted, the RFID tag reading operation 134 may be selected again (135). The result of the RFID tag reading operation 136 (e.g., tag information 82) is transferred to the handheld terminal and may be stored in the memory 72 of the handheld terminal. The result of the RFID tag reading operation 136 may be stored in a repository of the RFID reader 30.

During the steps 132 and 136, the user may select the step 130 so that the system 2 may return to the initial step 130 (e.g., 140) and the user will collect barcode and RFID tag information. The system 2 may automatically repeat the steps 130, 132, 136, and 140.

If the user selects the association operation 142, the user associates the barcode information 80 obtained at step 132 and the RFID tag information 84 obtained at step 134, on the handheld terminal using the user interface 60. The system 2 may automatically start the association operation 142 after obtaining the barcode information 80 and the RFID tag information 82. The association operation 142 may be done using the RFID tag and barcode information stored in the memory 72. The user may associate additional information with the barcode information, the RFID tag information, and/or the association result.

The result of the association is sent to the server 100 and stored in the database 102 of the server (144). The user may finish the RFID and barcode association process 146 when the association operation 142 is implemented on all of the RFID tags and the barcodes.

Figure 6:
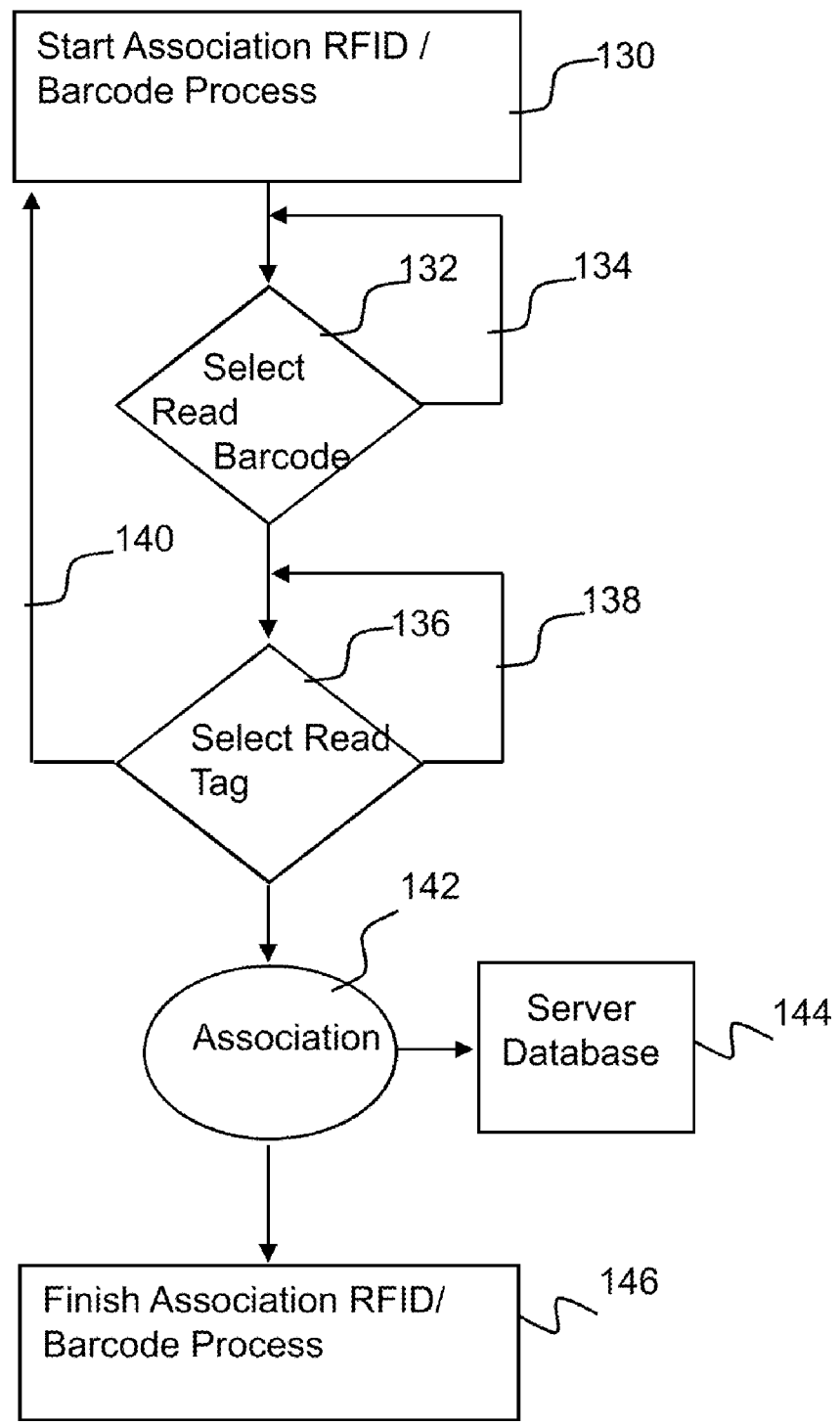
FIG. 6 is a flow chart illustrating a RFID/barcode association process in accordance with an embodiment of the present invention.

In FIG. 6, the barcode reading operation 132 is implemented prior to the tag reading operation 136. However, tag reading operation 136 may be activated prior to the barcode reading operation 132.

In addition, the menu for the association RFID/barcode process of FIG. 6 may include a selection of the adjustment of the RFID antenna power.

Figure 7:
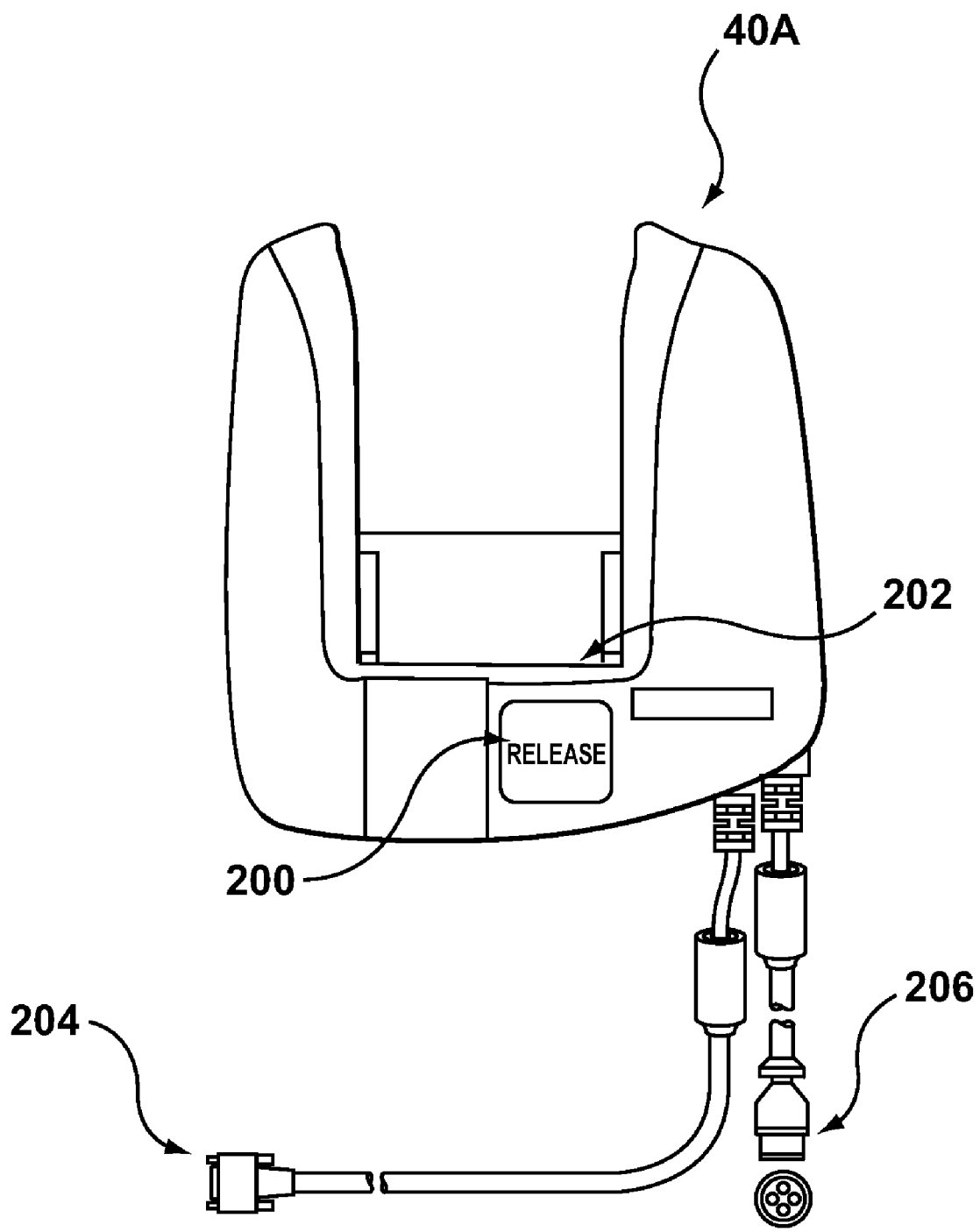
FIG. 7 is a diagram illustrating one example of the docking station of FIGS. 1-2.

Referring to FIG. 7, one example of the docking station 40 is described. The docking station 40A of FIG. 7 is one example of the docking station 40 of FIGS. 1-2. The docking station 40A includes a switch 200 for connecting or disconnecting the handheld terminal 20 of FIGS. 1-2 from the docking station 40, an electrical signaling interface 202 for allowing communication with the handheld terminal 20 and supplying power to the handheld terminal 20 of FIGS. 1-2, a Rx/Tx communication and power supply connector 206 for communicating with the RFID reader 30 of FIGS. 1-2 and supplying power to the RFID reader 30, and a connector for connecting to an external power supply source (e.g., 220V). "200" in FIG. 7 corresponds to 100 of FIG. 1. "202" in FIG. 7 corresponds to "112" of FIG. 3. "204" in FIG. 7 corresponds to "114" of FIG. 3. "206" in FIG. 7 corresponds to "116" of FIG. 3. The electrical signaling interface 202 is coupled to the interface (e.g., 90 of FIG. 3) of the handheld terminal 20 when the handheld terminal 20 is docked into the docking station 40A. The Rx/Tx communication and power supply connector 206 is coupled to the interface (e.g., 120 of FIG. 3) of the RFID reader 30 via the cable 34 of FIGS. 1-2.

In another example, the handled terminal (20, 20A) may be used as a mobile, stand-alone terminal when scanning the barcode 12. In this example, the handled terminal (20, 20A) is docked into the docking station 40 after the barcode scanning process, in order to drive the RFID reader 30 and associate the barcode information 80 with the tag information 82.

Figure 8A:
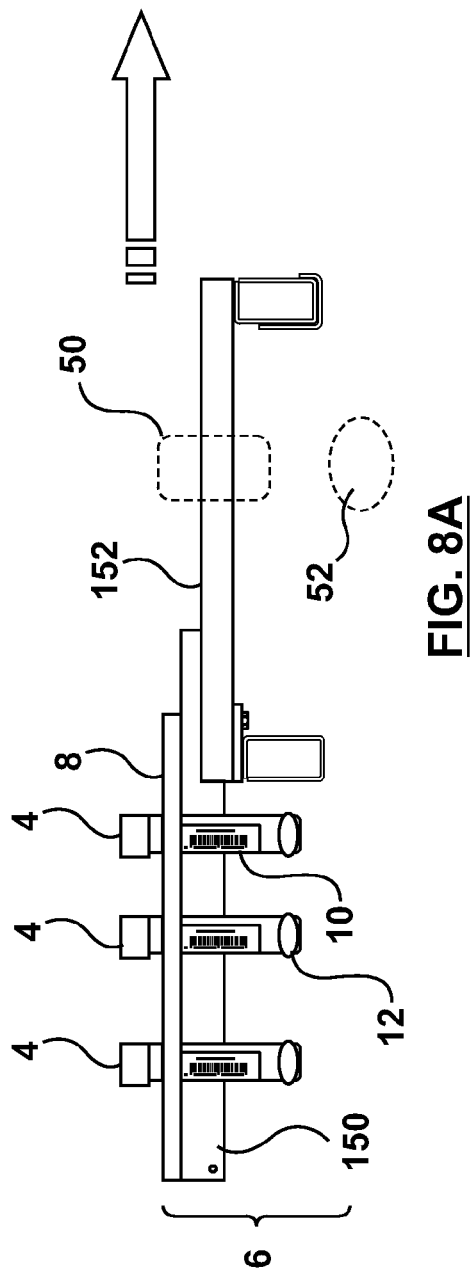
FIGS. 8A and 8B are schematic views of a slide system for positioning the physical object.
Figure 8B:
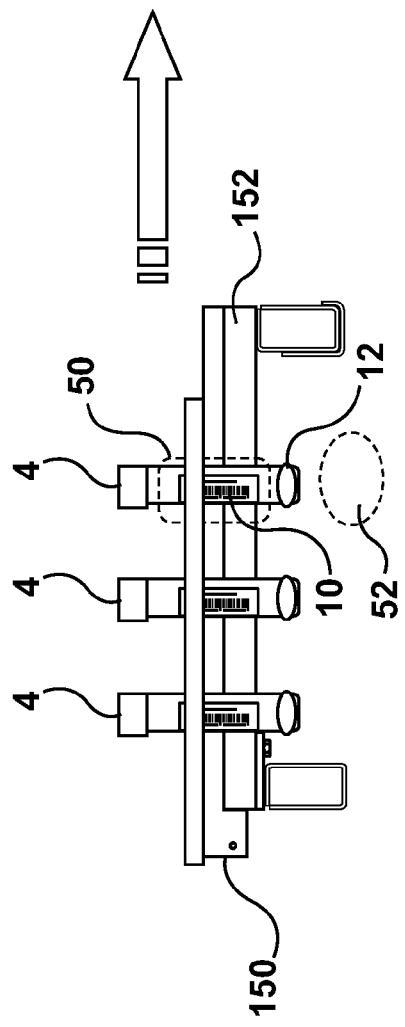

Referring to FIGS. 8A and 8B, a slide system for sliding the holder 8 is described in detail. As shown in FIGS. 8A and 8B, the storage 6 may have a frame 150 mounting the holders 8 and a slider system 152 for sliding the frame 150. The frame 150 is movably engaged with a slider of the slide system 150. The user manually push the frame 150 in order to locate the cryotube 4 in the holder 8 on the reading areas 50 and 52. This allows improving the ergonomics and productivity during the association.

In FIGS. 8A-8B, the holder 8 is moved in order to position each cryotube 4 in a specific position determined by the barcode reading area 50 and the RFID tag reading area 52. However, the sliding system 150 may have a sliding mechanism for changing the distance (Z of FIG. 5) between the docking station 40 and the holder 6, a sliding mechanism for changing the elevation of the holder 8, and a combination thereof.

According to the embodiments of the present invention, it is not required to position the cryotube 4 for the barcode scanning and the RFID reading. The system 2 can save time to acknowledge the location with no ambiguity, real time simultaneous operation and no misreading risk.

According to the embodiments of the present invention, the system 2 can adapt to different objects (distance to the object, aperture angle).

In addition, according to the embodiments of the present invention, the antenna reading distance is controlled, and adjusted (for example to a few centimeters) to make sure reading easily and not reading neighbor tags.

The systems and methods according to the embodiments of the present invention may be implemented by any hardware, software or a combination of hardware and software having the functions described above. The software code, either in its entirely or a part thereof, may be stored in a computer readable memory. Further, computer data signal representing the software code that may be embedded in a carrier waver may be transmitted via a communication network. Such a computer readable memory and a computer data signal are also within the scope of the present invention, as well as the hardware, software and the combination thereof.

One or more currently preferred embodiments have been described by way of example. It will be apparent to persons skilled in the art that a number of variations and modifications can be made without departing from the scope of the invention as defined in the claims.

It should be noted that the disclosure is not limited to the embodiment described and illustrated as examples. A large variety of modifications have been described and more are part of the knowledge of the person skilled in the art. These and further modifications as well as any replacement by technical equivalents may be added to the description and figures, without leaving the scope of the protection of the disclosure and of the present patent.

What is claimed is:

1. A system for managing a physical object, comprising:
   a RFID module for reading RFID tag information from a RFID tag in a RFID tag reading area;
   a handheld terminal being operable as a stand alone device, the RFID module and the handheld terminal being individually movable, the handheld terminal including:
   a barcode scanner for reading barcode information from a barcode in a barcode reading area;
   a driver for driving the RFID module; and
   a module for associating the barcode information with the RFID tag information transferred from the RFID module;
   a docking station releasably receiving the handheld terminal and providing an interface for communication between the handheld terminal and the RFID module; and
   a storage for holding a physical object having the barcode and the RFID tag to locate the physical object in the barcode reading area and the RFID tag reading area.

2. A system according to claim 1, wherein the RFID module comprises:
   a RFID antenna;
   a RFID reader for reading the RFID tag information from the RFID tag via the RFID antenna; and
   a first flexible cable for operably coupling the RFID reader to the RFID antenna.

3. A system according to claim 2, wherein the RFID reader comprises:
   a RFID writer for writing information to the RFID tag.

4. A system according to claim 2, wherein the handheld terminal controls an output power from the RFID reader to the RFID antenna via the docking station to change the RFID tag reading area.

5. A system according to claim 2, comprising:
   a second flexible cable for operably coupling the RFID reader to the docking station.

6. A system according to claim 1, wherein the docking station comprises:
   a terminal connectable to an external power source, and wherein the docking station supplies operation power to the RFID module.

7. A system according to claim 6, wherein the docking station supplies operation power to the handheld terminal.

8. A system according to claim 1, wherein the interface comprises:
   a first interface for communicating with the handheld terminal; and
   a second interface for communicating with the RFID module.

9. A system according to claim 8, wherein the docking station comprises:
   a terminal connectable to an external power source, and wherein the docking station supplies operation power to the handheld terminal via the first interface and supplies operation power to the RFID module via the second interface.

10. A system according to claim 1, wherein the docking station comprises:
    a switch for operably connecting or disconnecting the handheld terminal to the interface.

11. A system according to claim 1, wherein the handheld terminal comprises:
    an user interface, the user of the handheld terminal operating the handheld terminal and the RFID reader via the user interface.

12. A system according to claim 11, wherein the user of the handheld terminal associates the barcode information and the RFID tag information via the user interface.

13. A system according to claim 1, wherein the barcode reading area and the RFID tag reading area are predetermined.

14. A system according to claim 13, wherein the storage comprises:
  a moving mechanism for positioning the physical object in the barcode reading area and the RFID tag reading area.

15. A system according to claim 13, wherein the moving mechanism comprises:
  a slider for sliding the physical object.

16. A system according to claim 1, comprising:
  a server for communicating with the handheld terminal; and
  a database for storing the tag information, the barcode information and the association between the tag information and the barcode information.

17. A method of managing a physical object using a system having a RFID module, a handheld terminal having a barcode scanner and being operable as a stand alone device, the RFID module and the handheld terminal being individually movable, a docking station releasably receiving the handheld terminal and providing an interface for communication between the handheld terminal and the RFID module, and a storage for holding the physical object having a barcode and a RFID tag, the handheld device driving the RFID module via the docking station, comprising:
  determining a barcode reading area of the barcode scanner;
  determining a RFID tag reading area of the RFID module;
  determining a position of the physical object in the storage, based on the barcode reading area and the RFID tag reading area;
  operating the handheld terminal to read barcode information from the barcode in the position by the barcode scanner;
  operating the RFID module by the handheld terminal via the docking station to read RFID tag information from the RFID tag in the position; and
  operating the handheld terminal to associate the barcode information and the RFID tag information.

18. A method according to claim 17, comprising at least one of:
  docking the handheld terminal to the docking station prior to the barcode reading; and
  docking the handheld terminal to the docking station prior to the RFID tag reading.

19. A method according to claim 17, wherein the RFID module comprises an RFID reader and an RFID antenna, the method comprising:
  adjusting the output power from the RFID reader to the RFID antenna by the handheld terminal via the docking station.

20. A method according to claim 17, wherein the storage comprises a moving mechanism for positioning the physical object in the barcode reading area and the RFID tag reading area, the method comprising:
  locating the physical object by the moving mechanism.

21. A system for managing a physical object, comprising:
  a handheld terminal being operable as a stand alone device;
  an external RFID module for reading RFID tag information from a RFID tag in a RFID tag reading area, the RFID module and the handheld terminal being individually movable; and
  a docking station for releasably receiving the handheld terminal and providing an interface for communication between the handheld terminal and the RFID module, the handheld terminal including:
    a barcode scanner for reading barcode information from a barcode in a barcode reading area; and
    a processor for driving the RFID module and the barcode scanner and associating the barcode information with the RFID tag information transferred from the RFID module.

22. A system according to claim 21, wherein the RFID module comprises:
  a RFID antenna, and
  wherein the handheld terminal controls an antenna power of the RFID antenna via the docking station to change the RFID tag reading area.

23. A system according to claim 21, wherein the docking station comprises:
  a terminal connectable to an external power source, and
  wherein the docking station supplies operation power to the RFID module and supplies operation power to the handheld terminal.

24. A system according to claim 21, wherein the interface comprises:
  a first interface for communicating with the handheld terminal; and
  a second interface for communicating with the RFID module.

25. A system according to claim 24, wherein the docking station comprises:
  a terminal connectable to an external power source, and
  wherein the docking station supplies operation power to the handheld terminal via the first interface and supplies operation power to the RFID module via the second interface.

26. A system according to claim 21, comprising:
  a storage for positioning the physical object in the barcode reading area and the RFID tag reading area.

* * * * *